(12) United States Patent
Allen

(10) Patent No.: US 6,761,078 B2
(45) Date of Patent: Jul. 13, 2004

(54) ULTRASONIC FLOWMETER TRANSDUCER MOUNT

(75) Inventor: Charles R. Allen, Houston, TX (US)

(73) Assignee: Daniel Industries, Inc., Houston, TX (US)

( * ) Notice: Subject to any disclaimer, the term of this patent is extended or adjusted under 35 U.S.C. 154(b) by 0 days.

(21) Appl. No.: 09/944,268

(22) Filed: Aug. 30, 2001

(65) Prior Publication Data

US 2003/0041679 A1 Mar. 6, 2003

(51) Int. Cl.⁷ .............................................. G01D 21/00
(52) U.S. Cl. ..................................................... 73/866.5
(58) Field of Search ........................ 73/861.23, 861.25, 73/861.26, 861.27, 861.28, 861.29, 861.31, 866.5, 204.22

(56) References Cited

U.S. PATENT DOCUMENTS

| | | | | |
|---|---|---|---|---|
| 3,007,340 A | * | 11/1961 | Kraftson | 73/432 |
| 3,400,582 A | * | 9/1968 | Warner | 73/181 |
| 4,007,953 A | * | 2/1977 | Powell | 285/321 |
| 4,096,754 A | * | 6/1978 | Beveridge, Jr. et al. | 73/432 R |
| 4,452,090 A | * | 6/1984 | Kou et al. | 73/861.27 |
| 4,841,787 A | * | 6/1989 | Waterman | 73/866.5 |
| 4,858,470 A | * | 8/1989 | Kincaid et al. | 73/654 |
| 5,036,711 A | * | 8/1991 | Good | 73/861.66 |
| 5,065,892 A | * | 11/1991 | Lukez | 220/694 |
| 5,186,050 A | * | 2/1993 | Lagace et al. | 73/187 |
| 5,195,572 A | * | 3/1993 | Linden, Jr. et al. | 164/312 |
| 5,209,401 A | * | 5/1993 | Fiedrich | 237/8 C |
| 5,410,920 A | * | 5/1995 | Westwick | 73/866.5 |
| 5,481,197 A | * | 1/1996 | Sanders et al. | 324/690 |
| 5,727,498 A | * | 3/1998 | Hackler et al. | 116/206 |
| 6,145,392 A | * | 11/2000 | Kathan et al. | 73/866.5 |
| 6,397,683 B1 | * | 6/2002 | Hagenmeyer et al. | 73/861.18 |

* cited by examiner

*Primary Examiner*—Charles D. Garber
(74) *Attorney, Agent, or Firm*—Conley Rose, P.C.

(57) ABSTRACT

The present invention comprises an improved ultrasonic transducer mount including a removable union sleeve engaged with a transducer holder sleeve on the mount. The union sleeve has an outer diameter that engages an extractor tool for removal of the transducer and transducer holder from the mount. A retaining ring holds the union sleeve in place on the outside of the transducer holder sleeve.

15 Claims, 6 Drawing Sheets

ULTRASONIC FLOWMETER TRANSDUCER MOUNT

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to meters that measure the flow of a fluid. More particularly, the present invention relates to ultrasonic meters measuring fluid flow through a pipe. Still more particularly, the present invention relates to a structure for mounting transducers to an ultrasonic flow meter.

2. Description of the Related Art

After a hydrocarbon, such as natural gas, has been removed from the ground, it is often transported from place to place via pipelines. Very often, an owner or operator of a pipeline desires to accurately know how much gas is flowing through the pipeline. For example, where a billion standard cubic feet of natural gas flows through a single pipeline, even small percentage errors can result in serious miscalculations regarding the amount of gas flowing through the pipeline. Further, particular accuracy for the measurement is demanded when gas is changing hands, or "custody", because custody transfer applications often involve the exchange of money. Even so, an accurate meter is desirable for all phases of gas or fluid production, transportation, and distribution operations, and for off-shore platforms.

In response to the need for accurate gas flow measurement, ultrasonic flowmeters were developed. Ultrasonic flowmeters, also named sonic or acoustic flowmeters, revolutionized the gas industry because of their many advantages. For example, ultrasonic flowmeters are accurate over a large range of flow rates. Because ultrasonic gas flowmeters are non-intrusive, gas flows through the gas pipeline without encountering an increased pressure region. Consequently, considerable savings are achieved because the gas flows more easily in the pipe. In addition, ultrasonic flowmeters can also measure gas flow accurately despite changing gas composition.

Figure 1:
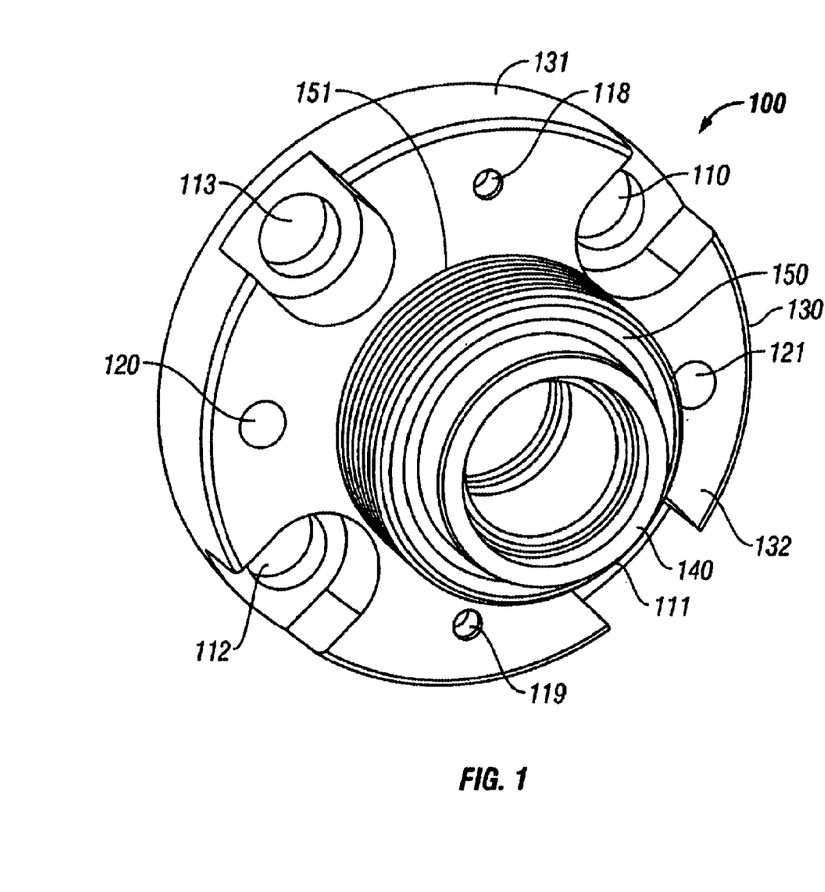
FIG. 1 is an illustration of a prior art transducer mount.

FIG. 1 shows a prior art ultrasonic transducer mount 100. The mount 100 includes a base 130 with a side surface 131 and a flat surface 132. Arcuately located on the base flat surface 132 are cap screw holes 110–113 for receiving cap screws 114–117 (not shown) respectively. Also located on base flat surface 132 are two jackscrew holes 120, 121 located 180° apart for receiving jackscrews (not shown). The jackscrews are used for removal of the mount from the meter housing. Also located on the base flat surface 132 are two mount cover holes 118, 119 located 180° apart for receiving the mount cover screws (not shown). Extending from the base 130 is a holder sleeve 140. The inner diameter (ID) of the holder sleeve 140 engages a transducer holder that holds a transducer (not shown). On the outside of holder sleeve 140 is union sleeve 150. Sleeve 150 is not removable from holder sleeve 140. On the outer diameter (OD) of union sleeve 150 are threads 151 for engagement with a union nut (not shown). The union nut is part of an extractor tool (not shown) for removal of the transducer holder and transducer.

In operation, the cap screws (not shown) attach the mount 100 to a meter housing (not shown). The transducer and transducer holder are then inserted into the holder sleeve 140. Once inserted, the transducer holder forms a fluid-tight seal at the joint with the holder sleeve. A mount cover (not shown) attaches to the mount base with screws that engage the mount cover holes 118, 119. The mount cover locks the transducer holder in place and prevents inadvertent disassembly during use and electrical connection to the transducer.

For removal of the transducer holder and transducer, first the mount cover is removed. The extractor tool (not shown) is then attached to the transducer mount. The extractor tool consists of an extractor tool valve (not shown) and a removable unit for isolation of the transducer holder and transducer from the transducer mount and meter housing. The extractor tool attaches to the transducer mount by the extractor tool valve union nut (not shown) engaging the union sleeve threads 151. Once engaged, the extractor tool makes an fluid-tight seal with the union valve seal. This seal allows removal of the transducer holder and transducer without releasing pressure from the meter housing and pipeline. The transducer and transducer holder are then removed from the holder sleeve 140 through the extractor tool valve and placed in a chamber in the extractor tool removable unit. Once the transducer holder and transducer are removed, the chamber is sealed from the holder sleeve. Once sealed, the transducer and transducer holder can be removed from the extractor tool.

For removal of the transducer mount 100, pressure must be vented from the housing and the cap screws (not shown) must be removed. Jackscrews are then inserted into jackscrew holes 120, 121. As the screws draw into the holes, they engage the meter housing surface. Further drawing the screws into the jackscrew holes forces the mount 100 out of engagement with the meter housing.

The large size of the current T-slot transducer mount provides certain drawbacks. Specifically, the current transducer mount causes problems with small meter housings. For example, the cast bosses for the very large OD transducer mounts greatly increase the casting weight of the housing casting because of the material needed at each transducer location boss to allow the mount to be attached. The housing transducer location bosses for the very large OD mounts also greatly increase the end to end length of the meter housing. The increased length is a major concern because the bore of the meter must be machined. The ability to machine a small ID over a very long length becomes harder as the length increases. This is true even if the bore is machined from each end. There are also cost issues concerned with the large size transducer mounts because of the large amount of material used.

It would be advantageous to design a transducer mount that is smaller in size than conventional designs, and that can be manufactured more inexpensively. Ideally, the new transducer mount would be compatible with existing extractor tools, transducers, and holders to facilitate a smooth transition to the new mount design. The new transducer mount would also allow for a smaller size meter housing than conventional meter housings. The smaller size meter housing would have a decreased casting weight and a decreased end to end length. It would also be advantageous to locate the transducer ports in the housing in the same location for different pressure rating transducer mounts. Despite the apparent advantages of such a transducer mount, to date no such mount has been commercially introduced.

SUMMARY OF THE INVENTION

The present invention comprises an improved ultrasonic transducer mount. Unlike prior transducer mounts, the improved transducer mount includes a removable union sleeve with an outer diameter (OD) that engages the inner diameter (ID) of the extractor tool union nut. A retaining ring holds the union sleeve in place on the outside of a transducer holder sleeve. The union sleeve and the retaining ring need only be used with the extractor tool for removal of the transducer.

According to an exemplary embodiment, the union sleeve fits over a holder sleeve on the mount. The holder sleeve has at least one flat surface that engages a similar configuration on the ID of the union sleeve. The flat surface(s) prevent(s) relative rotation between the union sleeve and holder sleeve after installation on the mount and during engagement and disengagement of the extractor tool.

The end of the union sleeve contacting the retaining ring includes a counter bore on the contacting face. The counter bore fully circumscribes the retaining ring when the union nut pulls the union sleeve against the retaining ring during engagement. This counter bore prevents inadvertent disassembly of the retaining ring from the groove if the extractor tool valve rotates as the union nut engages. Inadvertent disassembly occurs because rotation of the extractor tool valve rotates the union seal of the valve assembly and this rotation may un-spiral the retaining ring from its groove.

The design of the union sleeve, the counter bore on the end of the union sleeve, retaining ring, retaining ring groove, and the placement of the retaining ring groove on the mount are designed so that when the union nut and union seal of the extractor tool valve engage the mount, the retaining ring is compressed by the surface on the bottom of the counter bore on the end of the union sleeve and the end of the union seal. The compression of the retaining ring prevents the retaining ring from becoming canted within the groove as the pressure and other forces pull on the extractor tool assembly. By keeping the retaining ring perpendicular to the OD in the groove, the strength of the retaining ring and groove are greatly increased and wear is minimized.

With a removable union sleeve, the mount base can be smaller in size. This is because less clearance is required around the union sleeve threads for the cap screws that attach the mount base to the meter housing. With the mount base smaller, the mount cover is too big for direct attachment. To attach the mount cover, two mount cover retaining brackets connect to the mount base and are located 180° apart. The retaining brackets have screw holes for attachment of the mount cover by the mount cover screws. The retaining brackets also act as jackscrew holes eliminating the need for the holes on mount base. When the cover and mount base attachment means have been removed, the threaded holes in both of the retaining brackets receive the jackscrews. When the jackscrews tighten, the screws engage the meter housing and force the mount from the housing. The brackets thus also eliminate the need to provide additional holes solely for jackscrews.

Because the new design mount does not include a permanent OD surface for engagement with the extractor tool, the mount base can be made much smaller. The reduced mount size reduces cost by reducing the material needed. The reduced size also saves manufacturing costs with the ability to be investment cast. The smaller transducer mount also decreases the casting weight of the housing casting with the use of smaller housing transducer location bosses. The smaller transducer mount also decreases the end to end length of the small size meter housing. The smaller transducer mount also allows location of the transducer ports in the housing in the same location for different pressure rating transducer mounts. The smaller transducer mount, however, it still compatible with existing transducers and transducer holders.

Thus, the present invention comprises a combination of features and advantages which enable it to overcome various problems of prior devices. The various characteristics described above, as sell as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figures 2, 2A, 2B:
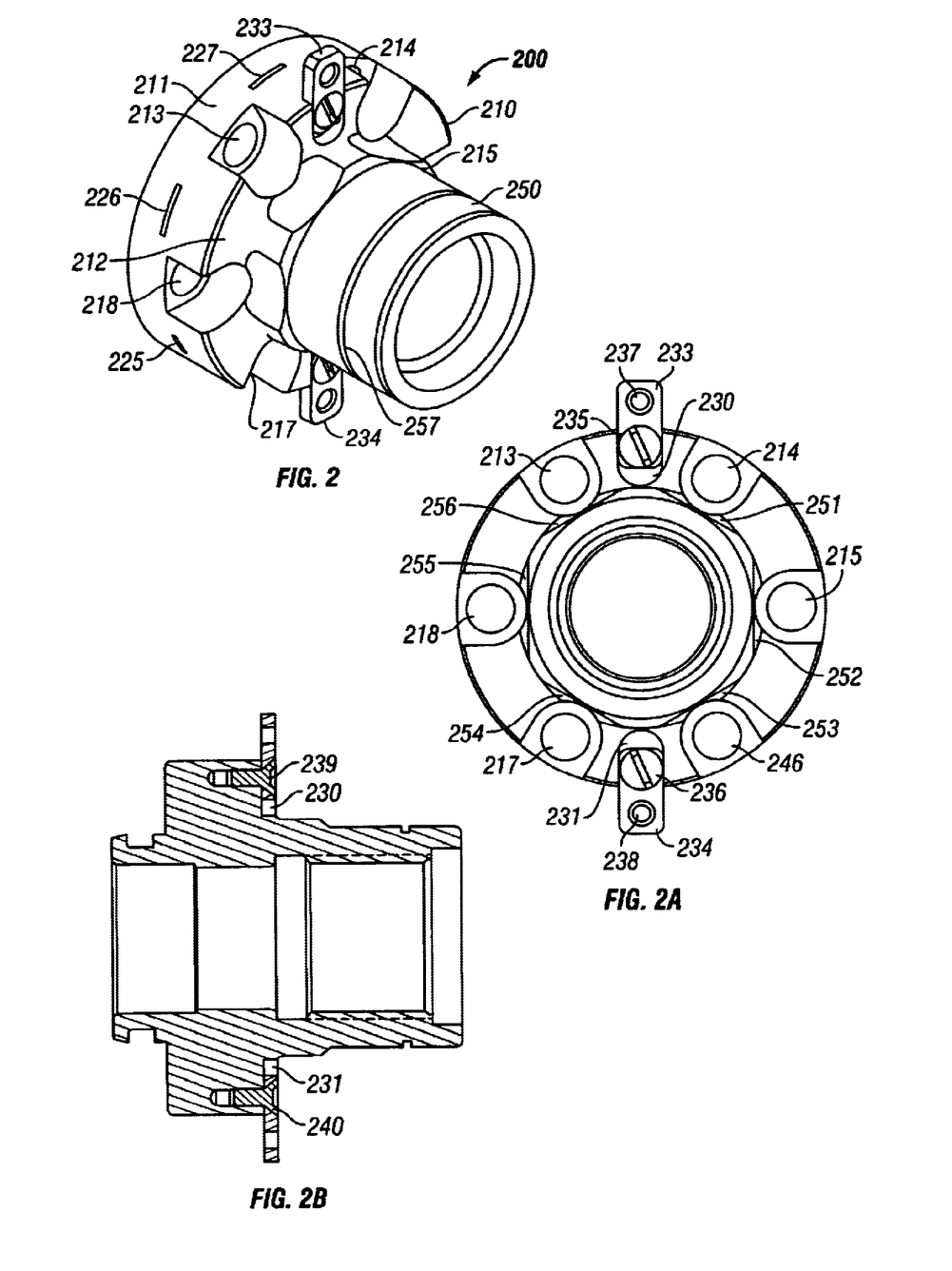
FIG. 2 is a perspective view of a transducer mount constructed in accordance with the preferred embodiment without a union sleeve attached.
FIG. 2A is a top view of the transducer mount of FIG. 2.
FIG. 2B is a cross-sectional view of the transducer mount of FIG. 2.

Referring initially to FIGS. 2, 2A, and 2B, transducer mount 200 constructed in accordance with the preferred embodiment will now be described. The mount 200 comprises a base 210 that includes a side surface 211 and a flat surface 212. Arcuately located in the base 210 are cap screw holes 213–218 for receiving cap screws (not shown). According to the preferred embodiment, slits 225–230 are made in the side surface 211 of base 210. Each slit has two opposing surfaces, one parallel to the flat surface 212 of the mount base 210 and the other angled to the first surface. The slits 225–230 preferably are sized to accommodate the flat blade of a screw driver or other pry bar tool to facilitate removal of the mount 200 from a housing (not shown). The slits 225–230 may not be suitable to completely remove the mount 200 from the housing, but preferably are sufficient to provide a gap between the mount 200 and the housing. The gap would then allow the use of a pry bar tool to pry the mount 200 completely free of the housing. The slits 225–230 thus eliminate the need for jackscrew holes in the mount 200.

Located on the mount base 210 are two mount cover bracket channels 230, 231 located 180° apart. Mount cover brackets 233, 234 fit within the mount cover bracket channels 230, 231 respectively. Mount cover brackets 233, 234 preferably include bracket holes 235, 236 and bracket mount cover holes 237, 238 respectively. Mount cover brackets 233, 234 eliminate the need for mount cover holes in the mount base 210. They also may be used as jackscrew holes, if necessary. Screws 239, 240 engage bracket holes 235, 236, respectively, and attach the brackets 233, 234 to the mount cover bracket channels 230, 231.

Holder sleeve 250 extends from mount base 210. Holder sleeve 250 sealingly engages with the transducer holder and transducer during operation. Located on the OD of holder sleeve 250 are flat surfaces 251-256. Also located on holder sleeve 250 is a groove 257 for engagement with a union sleeve retaining ring (not shown). In operation, cap screws (not shown) attach the mount 200 to a meter housing (not shown). The transducer and transducer holder are then inserted into the holder sleeve 250.

Figure 3:
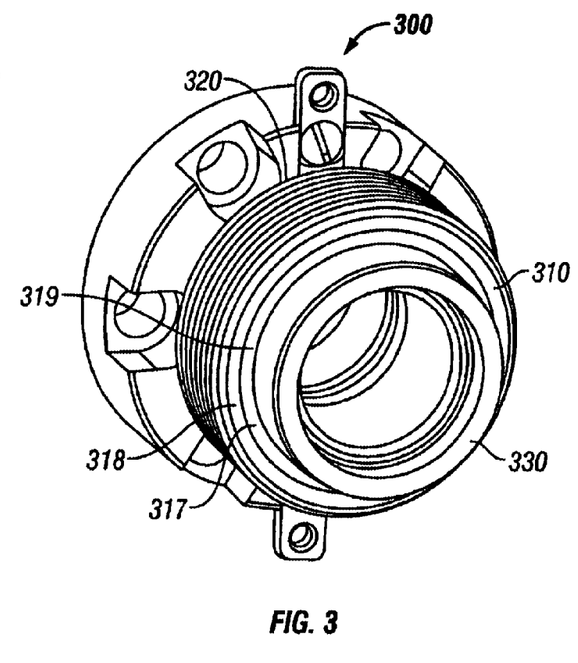
FIG. 3 is a perspective view of the transducer mount of FIG. 2 with a union sleeve attached.
Figure 3A:
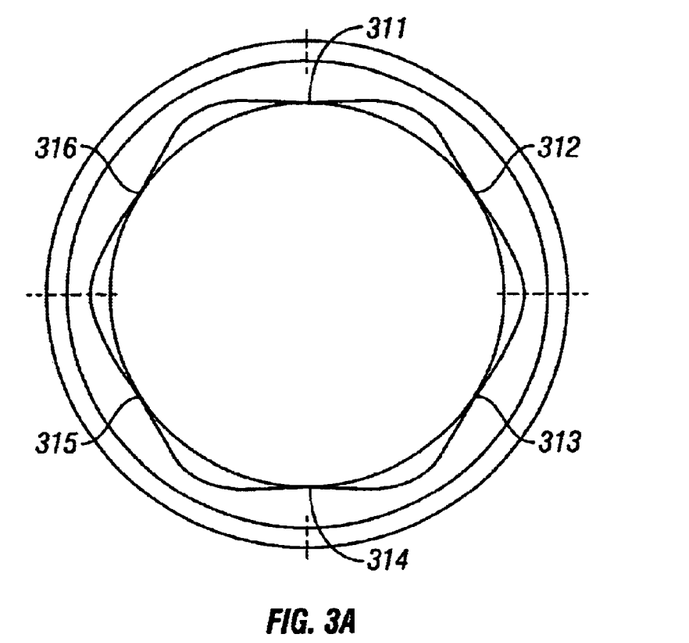
FIG. 3A is a top view of the union sleeve of FIG. 3.
Figure 3B:
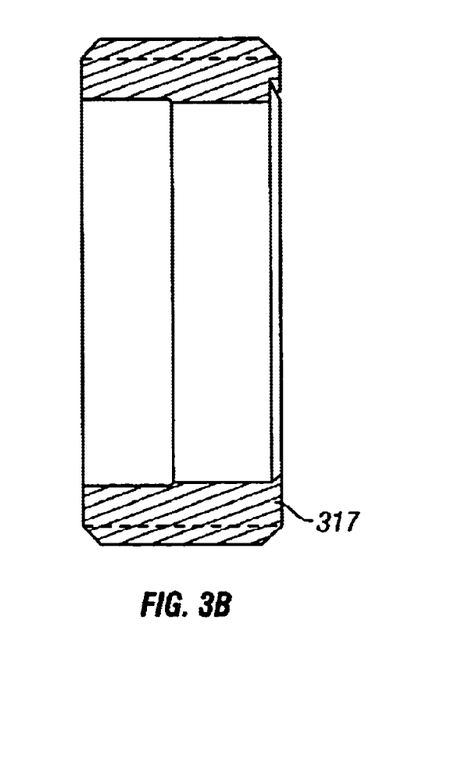
FIG. 3B is a cross-sectional view of the union sleeve of FIG. 3.

Referring now to FIGS. 3, 3A, and 3B, transducer mount 300 and removable union sleeve 310 constructed in accordance with the preferred embodiment will now be described. The union sleeve 310 slidingly engages holder sleeve 330. Union sleeve 310 is only placed on holder sleeve 330 when used with the extractor tool to remove the transducer and transducer holder. The ID of union sleeve 310 has flat surfaces 311–316 that engage the corresponding flat surfaces on the OD of the holder sleeve as shown in FIG. 2. The engagement of the flat surfaces 311–316 prevents relative rotation between the union sleeve and holder sleeve after installation on the mount and during engagement and disengagement of the extractor tool. The number and configuration of the flat surfaces may be altered without departing from the spirit of the present invention. The union sleeve has a counter bore 317 on the flat side 318 facing out from the mount base. Counter bore 317 engages retaining ring 319 held in place by retaining ring groove (shown in FIG. 2) on holder sleeve 330. The OD of union sleeve 310 has threads 320 that engage the ID threads of the union nut (not shown) of the extractor tool valve during removal of the transducer and transducer holder.

Figure 4:
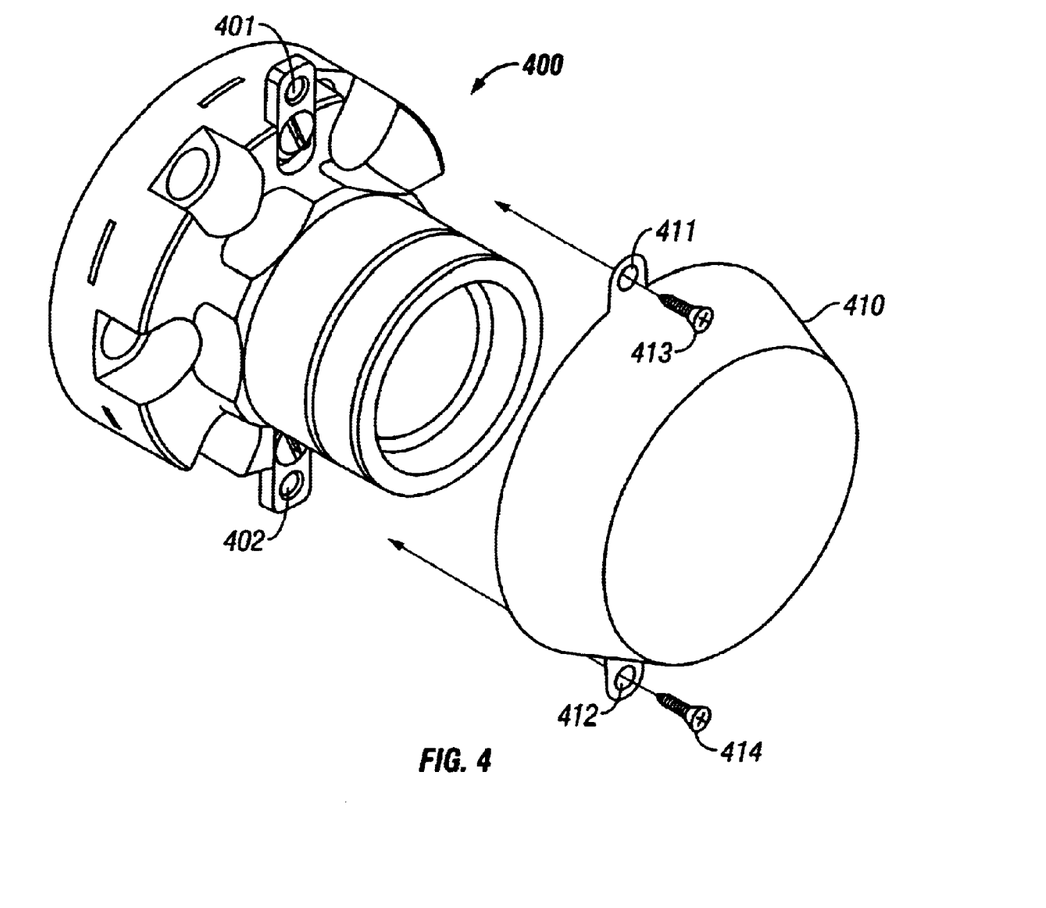
FIG. 4 is a perspective view of the transducer mount of FIG. 2 with the mount over shown.

Referring now to FIG. 4, transducer mount 400 and transducer mount cover 410 constructed in accordance with the preferred embodiment will now be described. The transducer mount cover 410 holds the transducer holder in place on the meter housing (not shown) and prevents inadvertent disassembly during use. The transducer mount cover 410 includes two holes 411, 412 located 180° apart on the edge of the cover 410. Screws 413, 414 attach the cover 410 to the mount 400 by engaging the mount cover holes 411, 412 and the bracket mount cover holes 401, 402.

Figure 5:
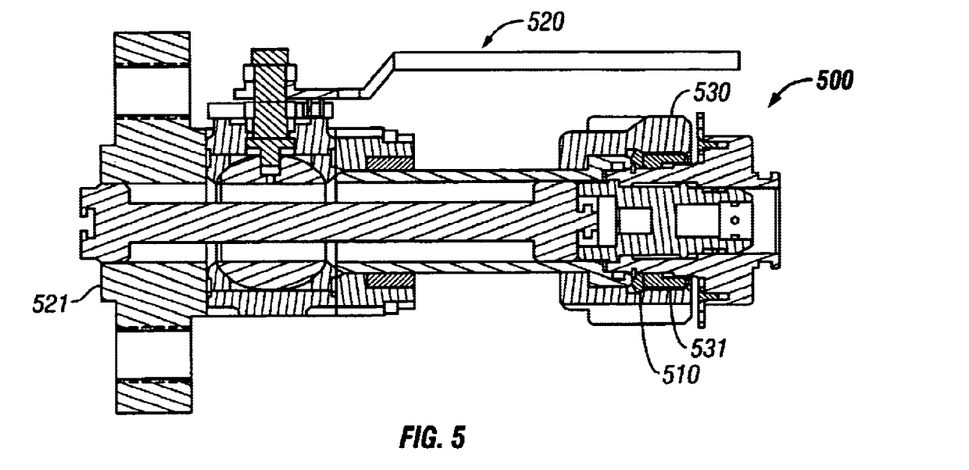
FIG. 5 is a cross-sectional view of a transducer mount extractor tool valve attached to a transducer mount constructed in accordance with the preferred embodiment.
Figure 5A:
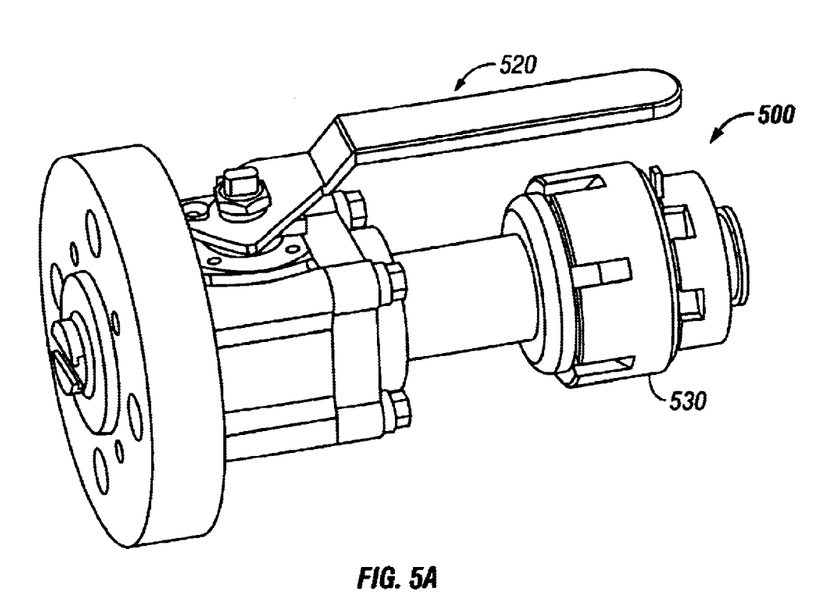
FIG. 5A is a perspective view of the transducer mount extractor tool valve of FIG. 5 attached to a transducer mount constructed in accordance with the preferred embodiment.

Referring now to FIGS. 5 and 5A, transducer mount 500 and extractor tool valve 520 attached to the union sleeve 510 constructed in accordance with the preferred embodiment will now be described. The extractor tool valve 520 has a union nut 530 disposed on one end. The union nut 530 has internal threads 531 and attaches to the union sleeve 510 by threading the union nut 530 onto the union sleeve 510. Once threaded, the union nut 530 and union sleeve 510 form a fluid-tight seal. This seal allows removal of the transducer holder and transducer without releasing pressure from the meter housing and pipeline. For removal, the transducer and transducer holder are extracted from the mount 500 through the extractor tool valve 520 and into a chamber in the extractor tool removable unit (not shown) that attaches to flange 521 on extractor tool valve 520. Once the transducer holder and transducer are removed and placed in the removable unit, the chamber is sealed from the mount 500. The transducer and transducer holder can then be removed from the extractor tool valve 520.

Figure 6:
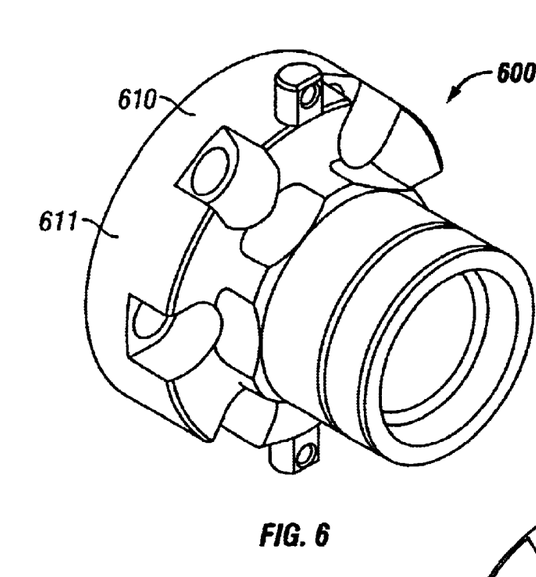
FIG. 6 is a perspective view of a first alternative embodiment transducer mount to the preferred embodiment shown in FIG. 2.
Figure 6A:
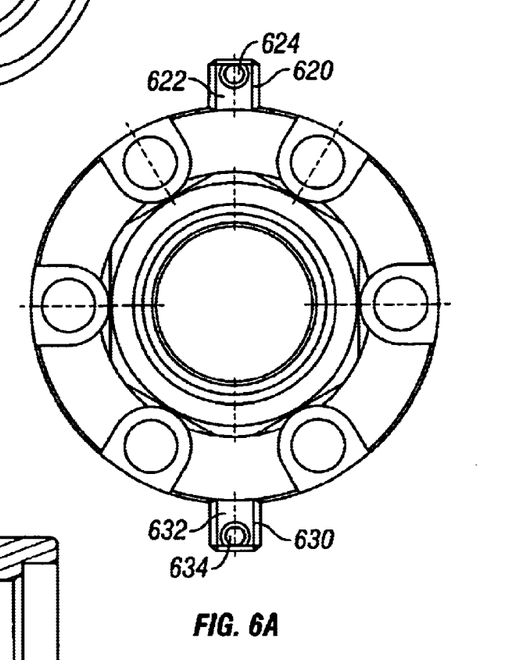
FIG. 6A is a top view of the first alternative embodiment transducer mount of FIG. 6.
Figure 6B:
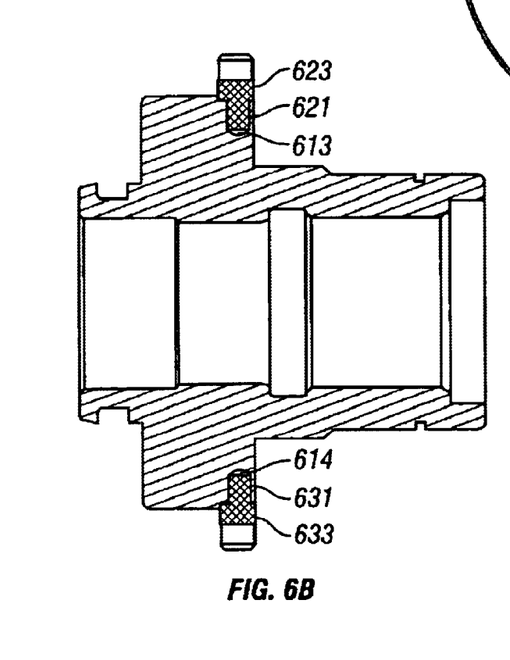
FIG. 6B is a cross-sectional view of the first alternative embodiment transducer mount of FIG. 6.

Referring now to FIGS. 6, 6A, and 6B, an alternative embodiment to the present invention will now be discussed. Mount 600 has the same features and operates the same way as the main embodiment except for the means attaching the mount cover to the mount. Located 180° apart on the mount base 610 are two retaining bosses 620, 630 pressed into holes 613, 614 in the side surface 611 of the mount base 610. The retaining bosses 620, 630 have a small end 621, 631 and a large end 622, 632. The retaining bosses 620, 630 have flat faces 623, 633 on the surface of the large end 622, 632. On this flat face 623, 633, boss mount cover attachment holes 624, 634 are machined prior to installation. The retaining bosses 620, 630 have knurls on the surface of the small ends 621, 631. The small ends 621, 631 are pressed into holes 613, 614 in the mount base side surface 611 with the boss mount cover attachment holes 624, 634 in the needed position. A fixture aligns the flat faces 623, 633 on the retaining bosses 620, 630 to the base of the mount 610. Alternatively, when the mount 600 is investment cast, the retaining bosses 620, 630 can be cast as part of the mount 600 and the boss mount cover holes 624, 634 machined into the cast bosses 620, 630.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A transducer mount comprising a base, a first sleeve extending from the base, and a removable second alcove slidingly engagable with the first sleeve, the removable second sleeve being prevented from complete rotation relative to the first sleeve when engaged with the first sleeve and the first sleeve adapted to retain a transducer when the second sleeve is removed.

2. The transducer mount of claim 1 wherein the base includes a top surface, at least one side surface, and a bottom surface.

3. The transducer mount of claim 2 wherein the transducer mount includes slots on the base top surface with slot boles extending through the base and screws fixedly engaging the slot holes for attaching the transducer mount to a housing.

4. The transducer mount of claim 2 wherein the base includes at least one slit on the at least one base side surface.

5. The transducer mount of claim 2 wherein the base includes channels on the base top surface with channel holes extending into the base and the transducer mount further comprising retaining brackets for engagement with the channels with a first hole through a first end and a second hole through a second end of the retaining brackets, first screws for attaching the bracket first ends to the base channels, a mount cover including attachment holes, and second screws for attaching the mount cover to the retaining bracket second end.

6. The transducer mount of claim 2 further comprising retaining brackets engaged with the mount base for retaining a mount cover.

7. The transducer mount of claim 6 wherein the retaining brackets engage channels on the base top surface, the channels having channel holes extending into the base.

8. The transducer mount of claim 7 wherein the retaining brackets comprise a first hole through a first end and a second hole through a second end, the mount further comprising first screws for attaching the bracket first ends to the base channels by engaging the channel holes and second screws for attaching the mount cover to the retaining bracket second end.

9. The transducer mount of claim 1 wherein the second sleeve outer diameter includes screw threads for attaching an extractor tool for removing a transducer and a transducer holder from the first sleeve inner diameter.

10. The transducer mount of claim 1 wherein the first sleeve outer diameter includes at least one first sleeve flat surface and the second sleeve inner diameter includes at least one second sleeve flat surface that engages the at least one first sleeve flat surface for preventing relative rotation between the first sleeve and the second sleeve.

11. The transducer mount of claim 1 wherein the transducer mount includes a groove located on the first sleeve outer diameter and a counter bore located on a second sleeve outer face, the outer face located on an end of the second sleeve opposite the base, and the transducer mount further comprises a retaining ring that engages both the groove and counter bore for retaining the second sleeve in engagement with the first sleeve.

12. The transducer mount of claim 1 further comprising retaining brackets engaged with the mount base for retaining a mount cover.

13. A transducer mount comprising:
   a base including a top surface, at least one side surface, a bottom surface, slots on the base top surface with slot holes extending through the base, and screws fixedly engaging the slot holes for attaching the transducer mount to a housing;
   channels on the base top surface with channel holes extending into the base;
   retaining brackets for engagement with the channels with a first hole through a first end and a second hole through a second end;
   first screws attaching the bracket first ends to the base channels;
   a mount cover including attachment holes and second screws attaching the mount cover to the retaining bracket second ends through the attachment holes;
   a first sleeve extending from the base including a first sleeve inner diameter and a first sleeve outer diameter with a groove and at least one first sleeve flat surface;
   a removable second sleeve slidingly engagable with the first sleeve including a second sleeve inner diameter with at least one second sleeve flat surface that engages the at least one first sleeve flat surface for preventing relative rotation between the first sleeve and the second sleeve, a second sleeve outer diameter with screw threads for attaching an extractor tool for removing a transducer and a transducer holder from the first sleeve inner diameter, and an outer face located on an end opposite the base with a counter bore; and
   a retaining ring that engages both the groove and counter bore for retaining the second sleeve in engagement with the first sleeve.

14. The transducer mount of claim 13 wherein the base includes at least one slit on the at least one base side surface.

15. A transducer mount comprising:
   a base comprising a top surface, at least one side surface, a bottom surface, slots on the base top surface with a slot hole extending through the base, screws fixedly engaging the slot holes and the housing, and at least one slit on the at least one base side surface;
   channels on the base top surface with screw holes extending into the base;
   retaining brackets for engagement with the channels with a first hole through a first end and a second hole through a second end;
   first screws for attaching the brackets to the channels by fixedly engaging the first holes and the channel holes;
   a mount cover with attachment holes;
   second screws for attaching the mount cover to the retaining bracket by engaging the mount cover attachment holes and second holes;
   a first sleeve extending from the base top surface comprising a first sleeve inner diameter, a first sleeve outer diameter, at least one first sleeve flat surface arranged around and protruding from the first sleeve outer diameter, and a groove extending around the first sleeve outer diameter;
   a removable second sleeve slidingly engagable with the first sleeve comprising a second sleeve inner diameter, a second sleeve outer diameter, an outer second sleeve face located on an end of the second sleeve opposite the base, a counter bore located on the outer second sleeve face, at least one second sleeve flat surface located on the second sleeve inner diameter that engages the at least one first sleeve flat surface, and screw threads located on the second sleeve outer diameter; and
   a retaining ring engagable with the groove and second sleeve counter bore for retaining the second sleeve in engagement with the first sleeve.

* * * * *